United States Patent
Leushuis (10) Patent No.: US 11,382,323 B2
(45) Date of Patent: Jul. 12, 2022

(54) CENTRALIZED SYSTEM FOR DISTRIBUTING OLFACTORY TRIGGERS FOR OVIPOSITIONING TO INSECT BREEDING ENCLOSURES

(71) Applicant: Protix B.V., Dongen (NL)

(72) Inventor: Raymond Leushuis, Alphen (NL)

(73) Assignee: Protix B.V., Dongen (NL)

( * ) Notice: Subject to any disclaimer, the term of this patent is extended or adjusted under 35 U.S.C. 154(b) by 210 days.

(21) Appl. No.: 16/500,422

(22) PCT Filed: Apr. 4, 2018

(86) PCT No.: PCT/NL2018/050208
§ 371 (c)(1),
(2) Date: Oct. 3, 2019

(87) PCT Pub. No.: WO2018/186741
PCT Pub. Date: Oct. 11, 2018

(65) Prior Publication Data
US 2021/0274766 A1    Sep. 9, 2021

(30) Foreign Application Priority Data

Apr. 4, 2017 (NL) .................................... 2018643
Dec. 12, 2017 (NL) .................................... 2020054

(51) Int. Cl.
*A01K 67/033* (2006.01)
*A01M 1/02* (2006.01)
(52) U.S. Cl.
CPC ............. *A01M 1/02* (2013.01); *A01K 67/033* (2013.01); *A01M 2200/012* (2013.01)

(58) Field of Classification Search
None
See application file for complete search history.

(56) References Cited

U.S. PATENT DOCUMENTS 4,594,964 A    6/1986  Vargas
5,759,224 A *  6/1998  Olivier ................... C05F 17/05
                                                   71/9

(Continued)

FOREIGN PATENT DOCUMENTS

CA    2955867    1/2016
EP    0561666    9/1993

(Continued)

*Primary Examiner* — Peter M Poon
*Assistant Examiner* — Morgan T Barlow
(74) *Attorney, Agent, or Firm* — N.V. Nederlandsch Octrooibureau (57) ABSTRACT

The present invention relates to a distribution system for distributing an olfactory attractant that stimulates ovipositioning of insects, comprising a central receptacle such as a container for holding an olfactory attractant and/or for holding a source of olfactory attractant, a delivery system comprising tubes, pipes and/or ducts, said tubes, pipes and/or ducts coupled to the receptacle and ending at locations where ovipositioning is desired, for delivering a liquid or gas from the receptacle such as a container to said locations, and a driver system for moving the attractant through the delivery system from the receptacle such as a container to said locations. The invention also relates to a method for stimulating ovipositioning of insects, such as black soldier flies, comprising delivering olfactory attractant from a receptacle such as a container to multiple ovipositioning areas via a driver system, said ovipositioning areas preferably located in a cage for insects.

8 Claims, 4 Drawing Sheets

(56) References Cited

U.S. PATENT DOCUMENTS

| | | | | |
|---|---|---|---|---|
| 6,130,084 | A * | 10/2000 | Endencia | A01K 67/033 119/6.5 |
| 6,244,213 | B1 * | 6/2001 | Tedders | A01K 67/033 119/6.6 |
| 6,990,768 | B1 * | 1/2006 | Boston | A01M 1/02 119/69.5 |
| 8,733,284 | B2 | 5/2014 | Courtright | |
| 2006/0086037 | A1 * | 4/2006 | Roberts | A01M 1/12 43/107 |
| 2007/0218804 | A1 * | 9/2007 | Allan | A01K 49/00 449/4 |
| 2011/0139075 | A1 * | 6/2011 | Shapiro Ilan | A01K 67/033 119/6.5 |
| 2013/0081573 | A1 * | 4/2013 | Chen | A01K 67/033 119/6.5 |
| 2014/0020630 | A1 * | 1/2014 | Courtright | A01K 67/033 119/6.6 |
| 2014/0123902 | A1 * | 5/2014 | Kitazumi | C05F 3/06 119/6.5 |
| 2014/0261188 | A1 | 9/2014 | Chin | |
| 2015/0122182 | A1 * | 5/2015 | Aldana | A01K 67/033 119/6.6 |
| 2016/0270378 | A1 * | 9/2016 | Chen | A01K 67/033 |
| 2018/0049417 | A1 * | 2/2018 | Leo | A23K 20/163 |
| 2018/0049418 | A1 * | 2/2018 | Leo | A21D 2/34 |

FOREIGN PATENT DOCUMENTS

| | | | |
|---|---|---|---|
| EP | 2846632 | 3/2015 | |
| GB | 2436199 A * | 9/2007 | A01K 67/033 |
| NL | 2011300 | 2/2015 | |
| WO | 2013166590 | 11/2013 | |
| WO | 2014171829 | 10/2014 | |
| WO | 2015013826 | 2/2015 | |
| WO | WO-2015027659 A1 * | 3/2015 | A01K 67/033 |
| WO | 2016011541 | 1/2016 | |
| WO | 2017007310 | 1/2017 | |

* cited by examiner

CENTRALIZED SYSTEM FOR DISTRIBUTING OLFACTORY TRIGGERS FOR OVIPOSITIONING TO INSECT BREEDING ENCLOSURES

FIELD OF THE INVENTION

The present invention in general relates to the field of large scale breeding of insects, such as black soldier flies, which select their location for ovipositioning (i.e. egg laying) according to olfactory cues. More in particular, the invention relates to a distribution system for distributing an olfactory attractant that stimulates ovipositioning of insects, in particular black soldier flies. Furthermore, the present invention relates to a method for stimulating ovipositioning of insects at a predetermined location, such as in a device designed to collect eggs. The invention also relates to the use of a distribution system for distributing an olfactory attractant that stimulates ovipositioning of insects.

BACKGROUND OF THE INVENTION

Insects are considered one of the most promising means for protein recovery and for organic residual recovery. Numerous species proposed for applications in human food and animal feed and pet food rely on olfactory cues to select the location for ovipositioning. The term "ovipositioning" refers to the laying of eggs, i.e. "to oviposition" here means to lay eggs. Prominent examples of species proposed for the indicated applications include the black soldier fly (*Hermetia illucens*), the house fly (*Musca domestica*), and the mealworm (*Tenebrio molitor* L.).

Methods improving the efficiency of egg collection from these species are particularly valuable for large scale production because the enormous quantity, delicacy, small size and stickiness of eggs. These challenges make it beneficial to collect eggs in a specific location since this simplifies collection operations and allows for efficient subsequent handlings. In the event that this location is a device designed to collect eggs, it will henceforth be referred to as an "ovisite" throughout this application.

The practice of using materials such as compounds or compositions of two or more compounds, such as fragrances comprising one or more chemical entities (henceforth, "attractants") to provide an olfactory cue for ovipositioning, is known as such in the art. Broadly, two strategies are applied to entice insects to lay eggs, or oviposition, in specific locations.

One known approach is to provide a location with physical properties desirable to the insect species being cultivated. Examples of egg collection interfaces are interfaces with a mesh, one or more slits or honey combs, which all are currently in use because many insects seek out such places to lay eggs. For example, in U.S. Pat. No. 4,594,964 an apparatus for rearing fruit flies is described, comprising a cage for housing fruit flies, and a perforated tube with a plurality of openings which stimulate cultured fly to oviposition for the purpose to maximize egg production. After ovipositioning, the eggs are readily collectable from the tube.

A further example of an egg collection interface is described in international patent application WO 2015/013826 and in patent EP 2846632 of the same applicant. A contained system is described for providing a reproductive habitat for *Hermetia illucens*. An oviposition chamber is placed inside a mating chamber, the oviposition chamber comprising a wire stopper as an entrance for gravid female black soldier flies, and the oviposition chamber being provided with corrugated cardboard blocks comprising openings as individual "flutes" in the cardboard for ovipositioning by the gravid flies.

An alternatively egg collection interface for gravid female insects is a food source for adult insects or their larvae, which is placed to attract gravid females to lay eggs in the proximity or even on or in such food.

US patent application US 2014/261188 describes an apparatus for breading fly larvae, comprising a fly habitat chamber, said fly habitat chamber comprising a larvae breeding part wherein flies may oviposition.

It is known that without offering gravid female insects an ovisite that is emitting an olfactory attractant, the egg capture yield at the location of the ovisite is essentially approaching zero. Olfactory attractant molecules escaping from an ovisite is a prerequisite for enticing gravid insects to oviposition at such a preselected and desired location. Approaches that make use of an attractant, e.g. an olfactory attractant, attempt to entice ovipositioning at a location that has desirable physical properties, like those described here above. One approach is to place an ovisite above a reservoir containing an attractant such as for example a container with an open air-exposed top containing the attractant within the cage in which the gravid insects are kept. More specifically, within the breeding environment, such as a cage, a dose of attractant is placed beneath the ovisite, and the odour that it produces entices gravid females to lay eggs in the ovisite above it. When the ovisite is ready for harvest, it is removed from the breeding environment.

The patent NL2011300C discloses the application of an ovisite with an attractant passing through it, but does not disclose how that attractant should be applied.

In patent EP2846632, a location for ovipositioning inside a mating chamber for black soldier flies is described, the location for ovipositioning being an oviposition chamber comprising a top drawer with a plurality of vertical flutes or tubes for receiving the eggs, the top drawer having openings in the bottom part, the bottom part positioned above a lower drawer comprising an attractant for attracting gravid black soldier flies. The attractant emerges into the mating chamber through the flutes or tubes of the oviposition chamber, thereby attracting the gravid female flies towards the location for ovipositioning.

In international patent application WO2016/011541, a continuous production system for culturing dipteran insects is described, comprising an ovipositioning chamber consisting of a rectangular tray with risers that suspend a honeycomb structure above an odoriferous attractant, i.e. an ovipositioning attractant, which resides in the bottom of the tray. Gravid female black soldier flies are attracted by the ovipositioning attractant and lay eggs on said honeycomb structure.

In another embodiment described in the above mentioned patent NL2011300C, the breeding environment and a rearing environment are placed adjacent to each other, with the rearing environment containing feed that emits an attractive odour, i.e. the ovipositioning attractant, or olfactory attractant. Between the breeding and rearing environments is a permeable ovisite through which the attractive odour passes, enticing gravid insects to lay eggs in the ovisite. The intention of such designs is that when the eggs hatch, the larvae will crawl to the rearing environment with the feed.

However, a reservoir of attractant such as a receptacle, e.g. a container, a tray, a cup, etc., with at least an open top side for allowing olfactory attractant to enter the air above the reservoir, which receptacle is either placed directly in the breeding environment (cages are considered henceforth), or directly placed outside said breeding environment, has certain disadvantages. This approach is for instance only suitable for small scale operations for example with a research focus, or for operations that otherwise do not intend to produce food products or feed products. Dosing attractant per each cage separately is only feasible by controlling the timing of placing each individual reservoir with attractant or source of attractant inside an individual cage and/or by controlling in individual cages the volume and surface of the attractant or source of attractant in the reservoir, when the number of cages is limited. However, in a large-scale production facility, the number of cages regularly is in the hundreds or thousands. This necessitates extensive (controlling of) dosing, cleaning and replacement of e.g. the individual receptacles with attractants and/or replacement of sources releasing such attractants, such as feed for larvae of the flies.

Additionally, the direct or near direct interaction of attractant sources with breeding insects presents risks of contamination of the insects and presents risks for contamination of the source of attractant, since all attractant sources disclosed in the literature (chicken feed, fly eggs, etc.) are suitable substrates for bacteria, mold, yeast, fungi, and are also attractive to other species of insects and pests.

Furthermore, many attractants and sources of attractants described in the literature make use of fermentation to produce the desired attractive odours. By placing attractant or a source of attractant in individual cages, the control over this fermentation process is significantly reduced. This has two negative repercussions. Firstly, the chances of a failure are increased with the number of doses since more doses can potentially fail. Secondly, doses that are failed are difficult to identify, since monitoring many doses is effort intensive.

In addition, when the receptacle containing an olfactory attractant or the receptacle containing the source of an olfactory attractant, is located in the cage or in each individual cage of a plurality of cages, it is nearly impossible to change such a receptacle for e.g. a new receptacle containing fresh olfactory attractant, and it is almost impossible to refill such a receptacle with for example a fresh source of olfactory attractant, without insects such as flies escaping from the cage, or it is at least very difficult and costly (e.g. a netting system might need to be installed or such) to replace or to refill such a receptacle. Replacing such a receptacle with a new one containing a fresh amount of olfactory attractant, or refilling a receptacle with olfactory attractant or a source thereof, is however a necessity in this set-up, since the strength of an olfactory attractant weakens over time as it ages, and the olfactory attractant or the source thereof dries out over time, and/or is used at a certain time point such that it has lost its effectivity in releasing olfactory attractant into the environment inside the cage.

Therefore, for the purpose of facilitating large-scale insect breeding and more specifically large-scale insect egg collection in an economically feasible and cost-effective manner, an improved method and improved means for collecting and harvesting insect eggs is highly desired in the field of industrial breeding of insects.

SUMMARY OF THE INVENTION

It is a goal of the present invention to take away the above mentioned disadvantages, or at least to provide a useful alternative to the state of the art.

The invention thereto provides a distribution system for distributing an olfactory attractant that stimulates ovipositioning of insects, in particular black soldier flies, comprising a source of olfactory attractant and/or an olfactory attractant contained in a reservoir such as a receptacle, further comprising a delivery system comprising tubes, pipes and/or ducts or the like, the delivery system being coupled to the reservoir, e.g. to the receptacle, and said delivery system ending at locations where ovipositioning is desired, the delivery system arranged for delivering a fluid, i.e. a liquid or gas, from the reservoir to said locations for ovipositioning, and the distribution system comprising a driver system for moving the olfactory attractant through the delivery system from the reservoir, e.g. the receptacle such as a container, to said locations for ovipositioning.

A first aspect of the invention relates to a distribution system for distributing an olfactory attractant that stimulates ovipositioning of insects, comprising:
  at least one central receptacle, such as a container, for containing olfactory attractant and/or for containing a source of olfactory attractant;
  a delivery system comprising tubes, pipes and/or ducts, wherein said tubes, pipes and/or ducts are coupled to the receptacle and ending at locations where ovipositioning is desired, for delivering a liquid or gas from the receptacle to said locations; and
  a driver system for moving the olfactory attractant through the delivery system from the receptacle to said locations.

The invention therewith provides a distribution system for delivering attractant to stimulate ovipositioning at a specific location that does not require applying the attractant source material separately at individual cages, nor expose the breeding insects to potential contaminants, offering as a consequence significant advantages in handling and hygiene in industrial operations. Herewith, the distribution system for distributing an olfactory attractant that stimulates ovipositioning of insects of the invention solves, amongst several further problems, the problem of the necessity to replace or refresh olfactory attractant or a source thereof on an individual cage by cage basis, as is at hand when olfactory attractant is supplied applying conventional methods known in the art, including placement of a receptacle with olfactory attractant or a source thereof in each individual cage. This way, by applying the distribution system of the invention, a source of olfactory attractant or an olfactory attractant is replaceable or can be refreshed centrally without interfering in the environment of the interior of the cages comprising the insect colonies. Thus, the distribution system of the invention allows for central refilling or changing the olfactory attractant or the source thereof during the breeding of insects such as flies, for example black soldier flies, without disturbing these insects. Moreover, applying the distribution system of the invention results in quick and easy and less laborious exchanging or refreshing of olfactory attractant at a central location, saving time and reducing the risk for contaminating a cage since there is no necessity to enter or touch the interior of the cage during replacement or refreshing olfactory attractant.

The reservoir is preferably a discrete space, for example a receptacle such as a container, according to the invention, but in an alternative embodiment the olfactory attractant is derived or retrieved from a specific room or area.

Preferably, the reservoir is a receptacle such as a container, a can, a bucket, a jar, a barrel, a holder, a box, though any reservoir known in the art suitable for containing an olfactory attractant or a source thereof is suitable for application in the distribution system of the invention. The receptacle comprised by the distribution system of the invention is preferably a closed receptacle such as a container, wherein the receptacle is provided with a first opening for coupling, preferably air-tight coupling, the driver system of the distribution system of the invention, and wherein the receptacle is provided with a second opening for coupling, preferably air-tight coupling, the delivery system of the distribution system of the invention. A receptacle which is providing an environment which shields attractant and/or a source of attractant contained in the receptacle, for contacting the environment other than through the tubes, pipes and/or ducts of the delivery system, is preferred, according to the invention. This way, the risk for contaminating the contained attractant and/or source of attractant inside the receptacle with any microbe present in the receptacles proximity is reduced, to name one benefit of such closed receptacle. In one embodiment, the central receptacle comprised by the distribution system of the invention comprises a first opening for receiving an end portion of the tube, pipe and/or duct of the delivery system of the distribution system, for coupling the receptacle to the delivery system, according to the invention. In one embodiment, the central receptacle comprised by the distribution system of the invention comprises a second opening for receiving a connector or a coupling of the driver system of the distribution system, for coupling the receptacle to the driver system, according to the invention.

One benefit of the invention is that it removes the need to provide cage-wise dosing of attractant or of any source of attractant. This is achieved by means of a centralized reservoir such as a receptacle, containing attractant and/or containing a source of attractant, arranged for serving multiple cages simultaneously. In a preferred embodiment, only odour is delivered to the breeding cages, while the actual attractive material is well separated from the living flies, remaining in a receptacle, such as a container. By reducing the number of locations where amounts of attractant or sources of attractant are kept, and preferably by preventing exposure of attractant or sources of attractant to the air, it is also easier to monitor the attractant or sources of attractant effectively. Furthermore, the central receptacle of the distribution system of the invention is not necessarily located in the area or room wherein insects are bred (in e.g. breeding cages) and wherein gravid female insects are supposed to lay eggs at/in ovisites positioned at predetermined positions where attractant odour, i.e. olfactory attractant, is delivered by the distribution system of the invention. That is to say, a single central receptacle of the distribution system of the invention is for example located in a control room, such that olfactory attractant is centrally deliverable to at least one room comprising for example tens to hundreds to thousands of cages with insects, said cages comprising the locations where ovipositioning is desired.

A further advantage of the distribution system according to the invention is the reduced consumption of olfactory attractant and/or sources thereof, for supplying multiple cages with olfactory attractant at locations where ovipositioning is desired by using said distribution system. For example, in current open systems such as crates with a source of attractant located at the bottom, which crates are placed underneath an ovisite, more attractant is to be delivered by such crate in order to achieve the desired level of attractant in the proximity of the locations where ovipositioning is desired, e.g. the ovisites, when compared to the amount of attractant to be specifically delivered at a predetermined location by the distribution system of the invention. Thus, one of the many advantages achieved by the current invention is a saving of the required amount of attractant for reaching the same or even an improved level of effectively attracting gravid female insects, e.g. black soldier flies, to the desired location for ovipositioning.

In one embodiment, the distribution system according to the invention comprises the central receptacle, wherein said receptacle, which is for example a container, comprises an olfactory attractant and/or comprises a source of an olfactory attractant.

According to an embodiment, the attractant is contained in any receptacle suitable for containing a sufficient quantity of attractant intended for distribution to two or more breeding cages, according to the invention, preferably a sufficient quantity of attractant intended for distribution to several hundred or even several thousand breeding cages.

According to an embodiment, one or more sources of attractant are contained in any receptacle suitable for containing a quantity of source or sources of attractant capable of providing a sufficient amount of olfactory attractant intended for distribution to two or more breeding cages, preferably tens to several hundreds of cages, such as twenty to hundred cages or such as between thirty and eighty cages, according to the invention. This way, the receptacle containing the attractant or containing the source of attractant acts as a reservoir of attractant to be distributed to the two or more breeding cages in a predetermined period of time at a predetermined dose such as a continuously supplied steady dose of attractant or a fluctuating dose for example during certain time intervals, as the case may be, according to the invention. Preferably, the attractant supplied in each of the two or more breeding cages by the system for distributing an olfactory attractant of the invention, is supplied at a constant dose, preferably continuously, at least during the time gravid insects are present in the breeding cages, according to the invention. One or multiple sources of attractant are used in the receptacle if needed, to ascertain the provision of the required quantity of attractant over time for distribution to the two or more cages, according to the invention. The centralized attractant source may have systems in place to manage any fermentation or otherwise necessary process for the production of the olfactory cues for oviposition used to entice the insects to lay at a specified location.

In one embodiment, the delivery system comprised by the distribution system of the invention is a conveyance system. According to the invention, such conveyance system is preferably a system composed of tubes, pipes or other parts building up a ventilation system capable of carrying air or fluid with the olfactory attractant, such as a gas or a vapour comprising attractant, e.g. odour, released from a source of attractant present in the central receptacle.

In one embodiment, the distribution system according to the invention comprises the aforementioned driver system, wherein said driver system comprises means for pressurizing an olfactory attractant and/or pressurizing a source of olfactory attractant contained in the central receptacle, such as a pump, coupled to the receptacle.

In one embodiment, the distribution system according to the invention comprises the aforementioned driver system, wherein said driver system comprises means for providing an under pressure to an olfactory attractant and/or to a source of olfactory attractant contained in the receptacle, such as a suction system arranged at the locations where ovipositioning is desired.

In one embodiment, the driver system comprised by the distribution system for distributing an olfactory attractant of the invention comprises means for pressurizing a receptacle and the attractant and/or source of attractant contained therein, said means for example being a pump according to the invention. Preferably, the driver system is a pump. Such a pump is preferably capable of creating overpressure in the receptacle containing an attractant and/or a source of attractant, the pump arranged to push said attractant and/or the attractant emitted or released by said source of attractant out into the delivery system such as a conveyance system, according to an embodiment of the invention. In an embodiment, the driver system comprised by the distribution system for distributing an olfactory attractant of the invention, comprises a suction system that draws the attractant out of the centralized receptacle such as a container and through the delivery system such as a conveyance system. That is to say, the suction system is capable of creating under pressure in the receptacle containing an attractant and/or a source of attractant, to pull said attractant and/or the attractant emitted by said source of attractant out into the conveyance system, according to an embodiment of the invention. Preferably, the driver system comprised by the distribution system for distributing an olfactory attractant of the invention, is such a suction system, according to the invention.

Such aforementioned pump is for example centrally arranged, for instance coupled to the central receptacle of the distribution system of the invention, such as a container, but decentral solutions are conceivable too, wherein one or more pumps are arranged in the delivery system of the distribution system of the invention, or at ends thereof (for instance in or at the cages), according to the invention. The delivery system is preferably configured to drive air into the receptacle of the distribution system for distributing an olfactory, e.g. a container, to force attractant through the tubes, pipes and/or ducts of said delivery system, preferably at a controllable selected rate, according to the invention.

In one embodiment, the distribution system according to the invention comprises the delivery system, wherein said delivery system comprises a coupling configured for said delivery system being coupled to at least one cage, the cage(s) comprising or forming a location where ovipositioning is desired. Preferred are cages for breeding flies such as black soldier flies, which cages are provided with an ovisite, said ovisite then being the location where ovipositioning is desired, according to the invention.

In one embodiment, the distribution system according to the invention comprises the delivery system, wherein said delivery system comprises valves, in particular controllable valves. The valves are then for example provided in the tubes, pipes and/or ducts of the delivery system, for example at or near one end or at or near both ends of such tubes, pipes and/or ducts, according to the invention. Such a delivery system comprised by the distribution system of the invention, provided with valves is particularly suitable for controlling by the distribution system the specific time and duration of transporting olfactory attractant from the central receptacle to the locations where ovipositioning is desired, and furthermore for controlling the dosing of said olfactory attractant, according to the invention. Furthermore, a delivery system with valves according to the invention also enables to selectively diverge the delivery of olfactory attractant with regard to time and duration of delivery and/or with regard to the dosing of olfactory attractant on an individual cage by cage basis. That is to say, presence of valves for example in the pipes, tubes and/or ducts in the delivery system provides the opportunity to specifically supply each separate and individual location where ovipositioning is desired with the optimal dose of olfactory attractant at the optimal time and with the optimal duration, related to for example the age and stage, e.g. the average age and/or average stage, and/or the number and/or type of the insects kept in the proximity of said locations where ovipositioning is desired, such as gravid female insects, e.g. gravid female black soldier flies, for example kept in cages provided with an ovisite. This way, improved controlling of the delivery of attractant at locations where ovipositioning is desired provides a means to improve egg harvesting, contributes to the saving of attractant resources and increases the efficiency of the use of attractant, according to the invention.

A second aspect of the invention relates to a method for stimulating ovipositioning of insects, comprising the step of delivering olfactory attractant from a central receptacle such as a container to multiple ovipositioning areas via a delivery system.

In one embodiment, the method for stimulating ovipositioning of insects according to the invention comprises the step of delivering the olfactory attractant, wherein said delivering comprises pumping a liquid or gas through the delivery system with a driver system.

The distribution system of the invention is particularly suitable for application in the method of the invention.

Besides other benefits, the invention as described above enables breed operations to achieve considerable labour savings over the state of the art systems and methods. Additionally, the growth of bacteria, mould and fungus on the attractant in the cage is avoided under the present invention, resulting in increased hygiene in breeding systems.

A third aspect of the invention relates to the use of the distribution system for distributing an olfactory attractant that stimulates ovipositioning of insects according to the invention in breeding of insects, preferably black soldier flies, which select their location for ovipositioning according to olfactory cues. Preferably, the distribution system of the invention is used in the large scale breeding of insects, e.g. black soldier flies. In this regard, the term "large scale" here refers to the breeding, e.g. continuous breeding throughout the whole year, of colonies of insects in parallel in hundreds to thousands of breeding cages, each such cage encompassing for example between about 500 to 50.000 insects.

Use of a centralized distribution system for distributing an olfactory attractant that stimulates ovipositioning of insects according to the invention makes it possible to rapidly identify system flaws since the restriction of attractant to a single location, i.e. in for example the receptacle such as a container, reduces the number of instances where a failure can occur, such as for example a failure in the fermentation of chicken feed, which fermentation process provides the olfactory attractant to be distributed by the delivery system and driver system of the distribution system of the invention, wherein thus the chicken feed is the source of attractant in the distribution system according to the invention and applied in the method according to the invention.

In one embodiment, the use according to the invention implies that the olfactory attractant is distributed by the distribution system to a plurality of cages comprising gravid female insects and further comprising an ovisite, preferably between 10 cages and 2.500 cages, more preferably between 100 and 1.500 cages. For example, the distribution system of the invention is used such that olfactory attractant is distributed from the central receptacle to about 250 to 1.000 cages simultaneously, according to the invention, therewith providing an efficient large scale method of efficaciously producing insects for the purpose of harvesting insects, retrieving protein and/or fat and/or lipids thereof, etc.

The present invention is here above and here below described with respect to particular embodiments and with reference to certain examples but the invention is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the invention.

Furthermore, the various embodiments, although referred to as "preferred" are to be construed as exemplary manners in which the invention may be implemented rather than as limiting the scope of the invention.

The term "comprising", used in the claims, should not be interpreted as being restricted to the elements listed thereafter; it does not exclude other elements. It needs to be interpreted as specifying the presence of the stated features, integers, or components as referred to, but does not preclude the presence or addition of one or more other features, integers, or components, or groups thereof. Thus, the scope of the expression "distribution system comprising A and B" should not be limited to a distribution system consisting only of components A and B, rather with respect to the present invention, the only enumerated components of the distribution system are A and B, and further the claim should be interpreted as including equivalents of those components.

As used herein, the term "may" encompasses the word "can," and the term "may be" encompasses the words "is" or "are," depending on context. Furthermore, presence of the word "may" is intended to explain options for practicing or implementing the disclosure, without limitation.

BRIEF DESCRIPTION OF THE DRAWINGS

The invention will now be elucidated into more detail with reference to FIGS. 1 to 4 and the exemplifying comparative example.

DETAILED DESCRIPTION OF PREFERRED EMBODIMENTS

Figure 1:
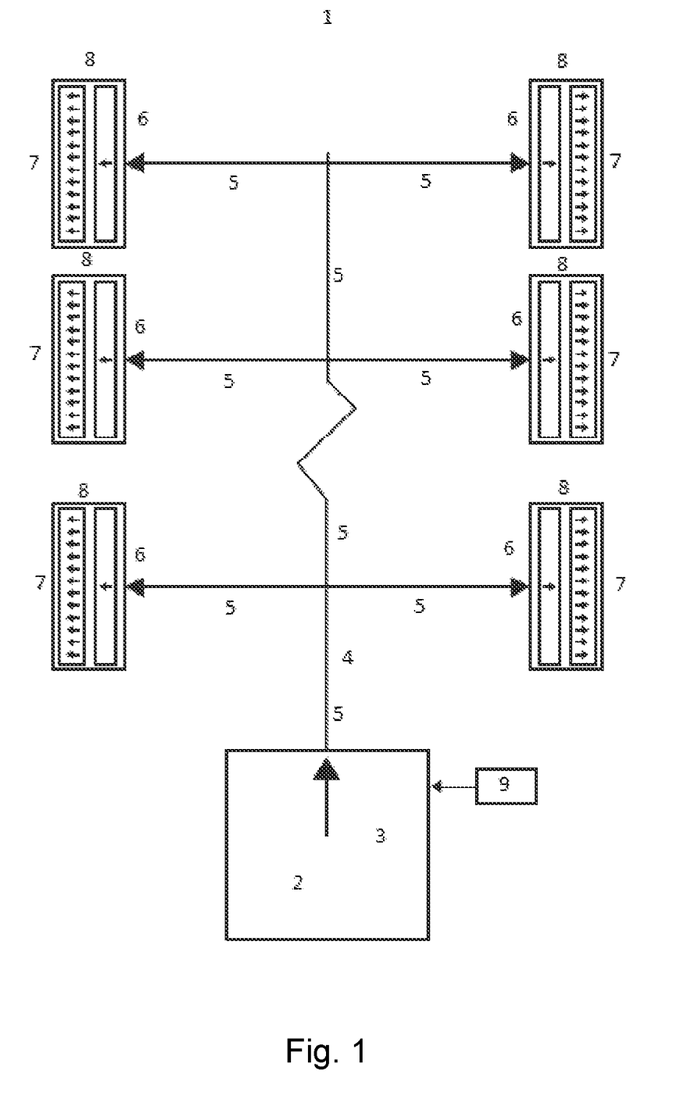
FIG. 1 shows a schematic view of a preferred embodiment of a distribution system according to the invention.

FIG. 1 shows a distribution system 1 for distributing an olfactory attractant 3 that stimulates ovipositioning of insects, comprising a receptacle 2 for containing an olfactory attractant 3 and/or a source of olfactory attractant 3, here embodied by container 2, for olfactory attractant 3, a delivery system 4 comprising tubes 5, coupled to the container 2 and ending at locations 6, formed by desired ovipositioning areas 7 in cages 8, for delivering the olfactory attractant 3 to said areas 7. The distribution system further comprises a driver system 9 for moving the attractant 3 through the delivery system 4 from the container 2 to the areas 7. Here, the distribution system 1 for distributing an olfactory attractant that stimulates ovipositioning of insects, e.g. black soldier flies, is arranged as a distribution system 1 comprising a delivery system 4 arranged as a tree structure composed of tubes 5, said tubes 5 coupling the central receptacle 2 to six individual cages 8. In this embodiment, the distribution system 1 comprises a receptacle 2 embodied by a container, said container provided with an olfactory attractant. The container is a closed container provided with an opening for receiving an outlet from the driver system 9 and with a second opening for receiving an inlet for a tube 5 of the delivery system 4.

Figure 2:
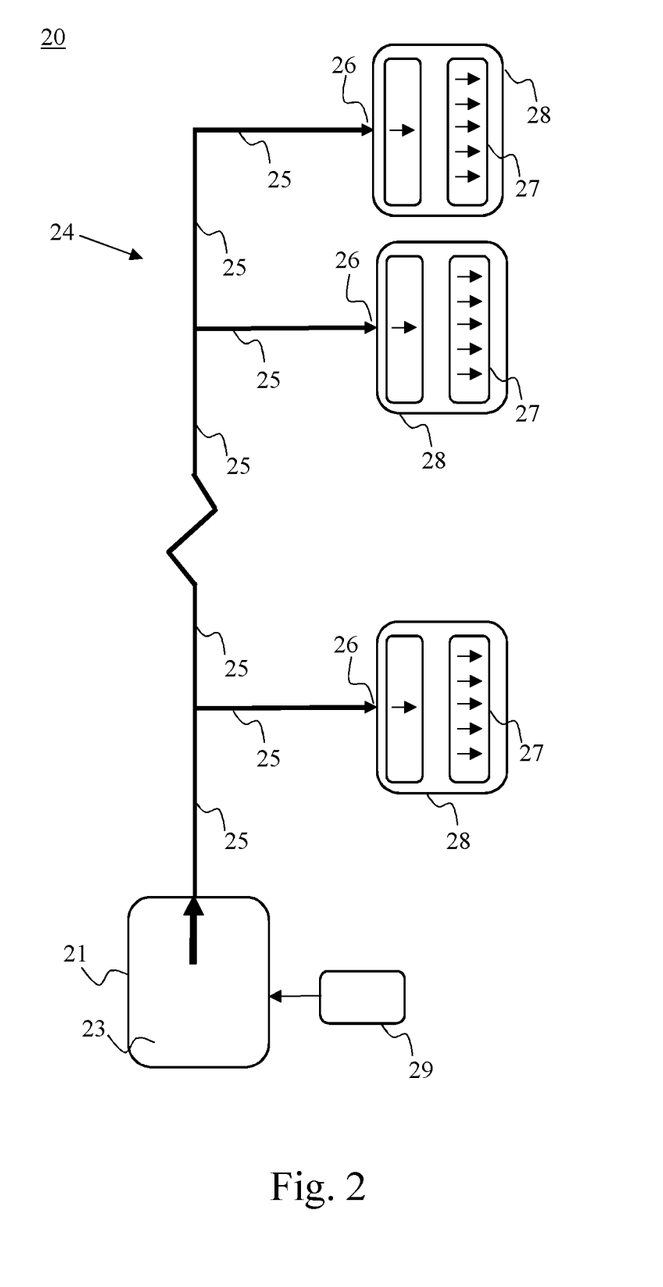
FIG. 2 shows a schematic view of a second preferred embodiment of a distribution system according to the invention.

FIG. 2 shows a distribution system 20 for distributing an olfactory attractant 23 that stimulates ovipositioning of insects, comprising a receptacle 21 for containing an olfactory attractant 23 and/or a source of olfactory attractant 23, here embodied by container 21, for olfactory attractant 23, a delivery system 24 comprising tubes 25, coupled to the container 21 and ending at locations 26, formed by desired ovipositioning areas 27 in cages 28, for delivering the olfactory attractant 23 to said areas 27. The distribution system further comprises a driver system 29 for moving the attractant 23 through the delivery system 24 from the container 21 to the areas 27. Here, the distribution system 20 for distributing an olfactory attractant that stimulates ovipositioning of insects, e.g. black soldier flies, is arranged as a distribution system 20 comprising a delivery system 24 arranged as a tree structure composed of tubes 25, said tubes 25 coupling the central receptacle 21 to multiple individual cages 28, of which three individual cages 28 are shown. In this embodiment, the distribution system 20 comprises a receptacle 21 embodied by a container, said container provided with an olfactory attractant. The container is a closed container provided with an opening for receiving an outlet from the driver system 29 and with a second opening for receiving an inlet for a tube 25 of the delivery system 24. Optionally, the distribution system 20 for distributing an olfactory attractant 23 that stimulates ovipositioning of insects comprises a coupling configured for said delivery system being coupled to at least one cage, the cage(s) comprising or forming a location where ovipositioning is desired. Optionally the distribution system 20 for distributing an olfactory attractant 23 that stimulates ovipositioning of insects comprises valves, in particular controllable valves.

Figure 3:
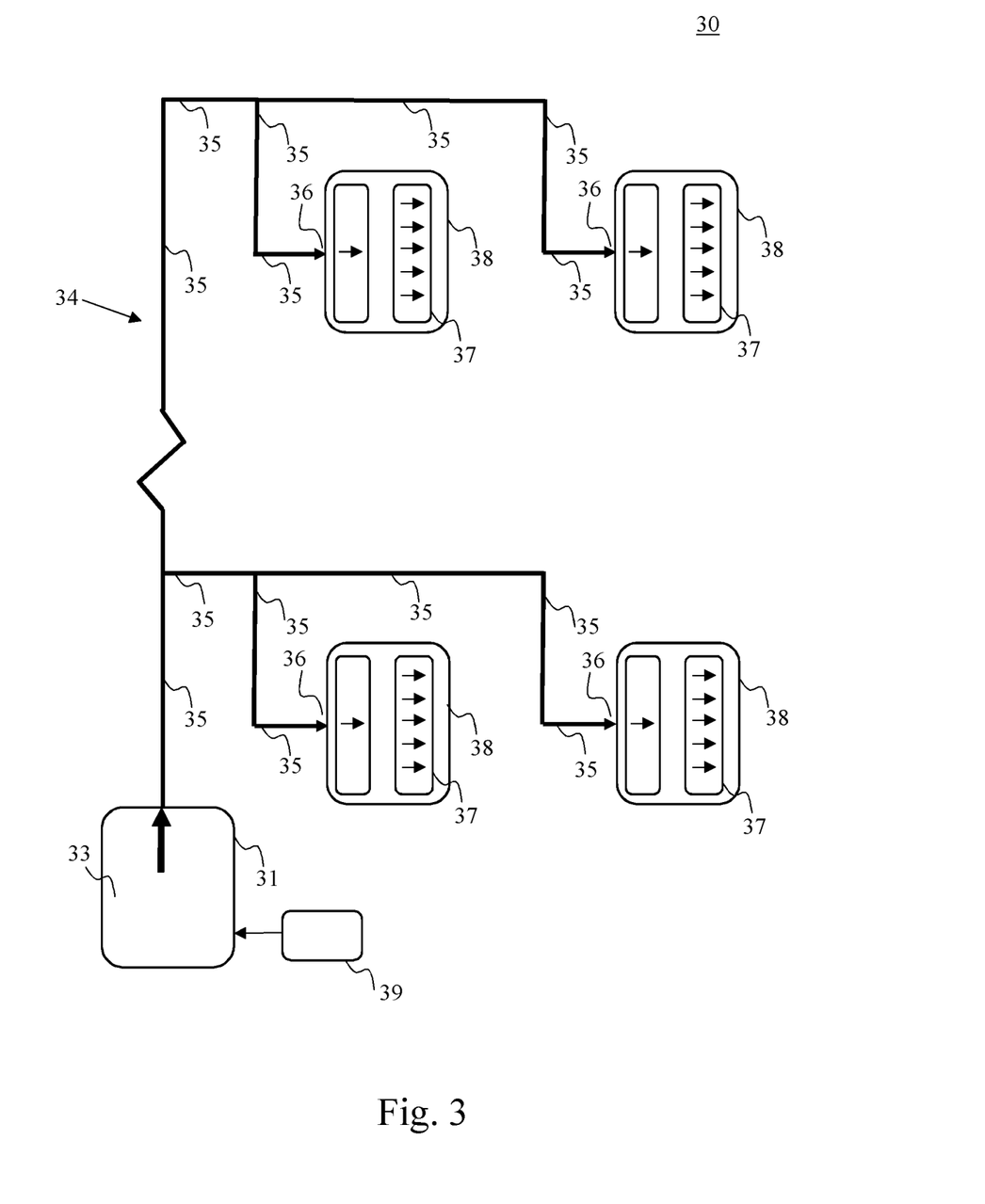
FIG. 3 shows a schematic view of a third preferred embodiment of a distribution system according to the invention.

FIG. 3 shows a distribution system 30 for distributing an olfactory attractant 33 that stimulates ovipositioning of insects, comprising a receptacle 31 for containing an olfactory attractant 33 and/or a source of olfactory attractant 33, here embodied by container 31, for olfactory attractant 33, a delivery system 34 comprising tubes 35, coupled to the container 31 and ending at locations 36, formed by desired ovipositioning areas 37 in cages 38, for delivering the olfactory attractant 33 to said areas 37. The distribution system further comprises a driver system 39 for moving the attractant 33 through the delivery system 34 from the container 31 to the areas 37. Here, the distribution system 30 for distributing an olfactory attractant that stimulates ovipositioning of insects, e.g. black soldier flies, is arranged as a distribution system 30 comprising a delivery system 34 arranged as a tree structure composed of tubes 35, said tubes 35 coupling the central receptacle 31 to multiple individual cages 38, of which three individual cages 38 are shown. In this embodiment, the distribution system 30 comprises a receptacle 31 embodied by a container, said container provided with an olfactory attractant. The container is a closed container provided with an opening for receiving an outlet from the driver system 39 and with a second opening for receiving an inlet for a tube 35 of the delivery system 34. In this embodiment, the delivery system 34 is arranged as a tree structure comprising a main branch, branched into sub-branches, wherein the sub-branches are further branched, each further sub-branch linked to an individual cage 38 at a position 36.

Figure 4:
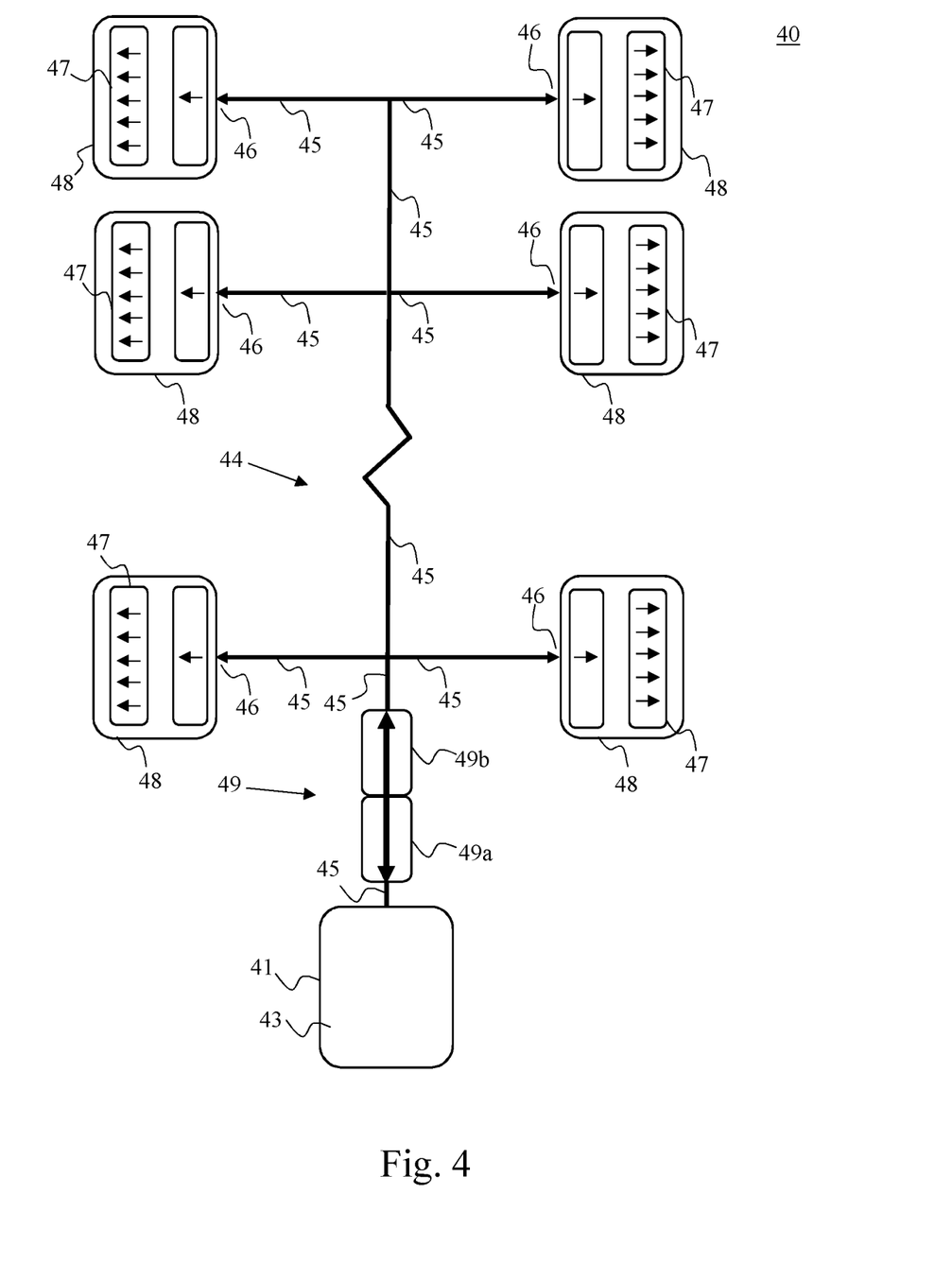
FIG. 4 shows a schematic view of yet an alternative preferred embodiment of a distribution system according to the invention.

FIG. 4 shows a distribution system 40 for distributing an olfactory attractant 43 that stimulates ovipositioning of insects, comprising a receptacle 41 for containing an olfactory attractant 43 and/or a source of olfactory attractant 43, here embodied by container 41, for olfactory attractant 43, a delivery system 44 comprising tubes 45, coupled to the container 41 and ending at locations 46, formed by desired ovipositioning areas 47 in cages 48, for delivering the olfactory attractant 43 to said areas 47. The distribution system further comprises a driver system 49 for moving the attractant 43 through the delivery system 44 from the container 41 to the areas 47. The distribution system comprises the driver system 49, wherein said driver system comprises means 49a for providing an under pressure to the olfactory attractant 43 and/or to the source of olfactory attractant 43 contained in the receptacle 41, such as a suction system 49a coupled to the receptacle 41, and wherein said driver system 49 comprises means 49b for pressurizing the olfactory attractant and/or a source of olfactory attractant, such as a pump 49b coupled to the suction system 49a, which in turn is coupled to the receptacle. Optionally, the distribution system 40 for distributing an olfactory attractant 43 that stimulates ovipositioning of insects comprises a coupling configured for said delivery system being coupled to at least one cage, the cage(s) comprising or forming a location where ovipositioning is desired. Optionally the distribution system 40 for distributing an olfactory attractant 43 that stimulates ovipositioning of insects comprises valves, in particular controllable valves.

In this embodiment, the distribution system 40 for distributing an olfactory attractant that stimulates ovipositioning of insects, e.g. black soldier flies, is arranged as a distribution system 40 comprising a delivery system 44 arranged as a tree structure composed of tubes 45, said tubes 45 coupling the central receptacle 41 to multiple individual cages 48, of which three individual cages 48 are shown. In this embodiment, the distribution system 40 comprises a receptacle 41 embodied by a container, said container provided with an olfactory attractant. The container is a closed container provided with an opening for receiving an inlet for a tube 45 of the delivery system 44. In this embodiment, the delivery system 44 is arranged as a tree structure comprising a main branch, branched into sub-branches, wherein each of the sub-branches are linked to an individual cage 48 at a position 46.

In one embodiment, the distribution system according to the invention thus comprises the delivery system, wherein said delivery system has a tree structure, such as for example the tree structure shown in FIG. 1 or the tree structure shown in FIG. 4.

In one embodiment, the distribution system according to the invention comprises the delivery system, wherein said delivery system is provided with tens to thousands of outlets for delivering olfactory attractant at the locations where ovipositioning is desired, preferably between 100 and 1.000 outlets. It is part of the invention that optionally these outlets are provided with a valve, preferably a controllable valve with regard to its open position and its closed position, such that the timing and duration of delivery of a predetermined amount and type of olfactory attractant is controllable at the individual cage to cage level.

Comparative Example

A distribution system of the invention, embodied by the distribution system 30 displayed in FIG. 3 and comprising an olfactory attractant that stimulates ovipositioning, was manufactured and the efficiency and efficacy of ovipositioning by gravid female black soldier flies at locations where ovipositioning was desired and where the olfactory attractant that stimulates ovipositioning was delivered, here at a predetermined location in a cage, was compared with the efficiency and efficacy of ovipositioning by gravid female black soldier flies in a conventional cage comprising a location where ovipositioning was desired. It was noticed that in the cages in which the distribution system of the invention delivered olfactory attractant that stimulates ovipositioning at locations where ovipositioning was desired, gravid female black soldier flies laid eggs at fewer locations in the cage, away from the locations where ovipositioning was desired, than gravid female black soldier flies kept in conventional cages without a distribution system of the invention. In such conventional cages, the flies laid a substantial number of eggs outside locations where ovipositioning was desired, such as a card box having a surface interface with a mesh or a honeycomb structure. In cages provided with a distribution system of the invention, the flies laid most eggs at the locations where ovipositioning was desired, such as a honeycomb structure, whereas substantially fewer eggs were laid elsewhere in the cages. In conventional cages which were not provided with an efficient system for distributing an olfactory attractant, and in cages provided with a distribution system of the invention, though without the driver system properly distributing attractant to the positions where ovipositioning was desired (e.g. by supplying insufficient amounts of attractant through the delivery system), a colony of insects such as black soldier flies produced less eggs compared to a similar colony of flies kept in a cage provided with the distribution system of the invention. Moreover, in said cages without proper delivery of olfactory attractant by a distribution system of the invention, or without such a distribution system at all, hardly any eggs where laid in the positions where ovipositioning was desired, here a card box with a honeycomb structure. Herewith, conventional systems without an efficient system for constant and controllable delivery of predetermined amounts of olfactory attractant at predetermined time points and time windows at positions in a cage for keeping insects such as black soldier flies, do not provide for a viable system for economical culturing of flies and harvesting of insect eggs at industrial scale. In contrast, in the comparative example, cages provided with the distribution system of the invention turned out to be highly beneficial for economically viable culturing at large scale of e.g. black soldier flies and collecting their eggs at positions where ovipositioning was desired. Furthermore, with the aid of the distribution system of the invention, it was found that cage to cage differences with regard to the position of ovipositioning and with regard to the number of laid eggs and with regard to the time window in which insects laid their eggs, were less and could be minimized compared to cage to cage differences for these parameters when conventional cages were applied, lacking the distribution system of the invention. Amongst others, these beneficially smaller cage to cage differences relate to the application of a central single source of olfactory attractant that stimulates ovipositioning of insects, according to the invention. Moreover, by applying a distribution system of the invention, ovipositioning of gravid flies bred simultaneously in separate cages is improvingly synchronized when compared to ovipositioning by colonies of insects bred in cages comprising a conventional system for distributing an olfactory cue.

The above outlined embodiments of FIGS. 1-4 and examples show examples only and are in no way limiting the scope of the invention, which is defined in the following claims.

The invention claimed is:

1. Distribution system for distributing an olfactory attractant that stimulates ovipositioning of insects to a plurality of cages where ovipositioning is desired, comprising:
   at least one central receptacle for containing and separating an odorant olfactory attractant and/or a source of an odorant olfactory attractant from the insects;
   a delivery system comprising tubes arranged between the at least one central receptacle and the plurality of cages, wherein said tubes are coupled to the central receptacle and the plurality of cages for delivering a liquid or gas from the central receptacle to said plurality of cages; and
   a driver system for moving the odorant olfactory attractant through the delivery system from the central receptacle to said plurality of cages,
   wherein the driver system comprises means for pressurizing the odorant olfactory attractant and/or the source of the odorant olfactory attractant contained in the central receptacle and coupled to the central receptacle for pushing the odorant olfactory attractant and/or the source of the odorant olfactory attractant into the delivery system.

2. The distribution system according to claim 1, wherein the driver system further comprises a suction system arranged at the plurality of cages where ovipositioning is desired for providing an under pressure to an odorant olfactory attractant and/or to a source of an odorant olfactory attractant contained in the central receptacle.

3. The distribution system according to claim 1, wherein the delivery system has a tree structure.

4. The distribution system according to claim 1, wherein the delivery system further comprises valves.

5. The distribution system according to claim 1, wherein the delivery system is provided with 100 to 1000 outlets for delivering the odorant olfactory attractant at the plurality of cages where ovipositioning is desired.

6. The distribution system for distributing an odorant olfactory attractant that stimulates ovipositioning of insects according to claim 1, wherein the insects select their location for ovipositioning according to olfactory cues.

7. The distribution system according to claim 6, wherein the odorant olfactory attractant is distributed by the distribution system to said plurality of cages comprising gravid female insects and further comprising an ovisite.

8. Method for stimulating ovipositioning of insects, comprising a step of delivering an odorant olfactory attractant from a central receptacle to a plurality of cages where ovipositioning is desired via a delivery system,
   wherein the delivery system comprises tubes arranged between the central receptacle and the plurality of cages, wherein said tubes are coupled to the receptacle and the plurality of cages, wherein the step of delivering the odorant olfactory attractant comprises pumping a liquid or gas through the delivery system with a driver system,
   wherein the driver system comprises means for pressurizing the odorant olfactory attractant and/or a source of odorant olfactory attractant contained in the receptacle and coupled to the receptacle for pushing the odorant olfactory attractant and/or the source of odorant olfactory attractant into the delivery system.

* * * * *